United States Patent
Yoshida et al.

(10) Patent No.: US 11,063,474 B2
(45) Date of Patent: Jul. 13, 2021

(54) WIRELESS POWER SUPPLY SYSTEM AND NON-TRANSITORY TANGIBLE COMPUTER-READABLE STORAGE MEDIUM

(71) Applicant: DENSO CORPORATION, Kariya (JP)

(72) Inventors: Ichiro Yoshida, Kariya (JP); Takafumi Ito, Kariya (JP); Hiroyuki Dosho, Kariya (JP)

(73) Assignee: DENSO CORPORATION, Kariya (JP)

( * ) Notice: Subject to any disclaimer, the term of this patent is extended or adjusted under 35 U.S.C. 154(b) by 165 days.

(21) Appl. No.: 16/408,863

(22) Filed: May 10, 2019

(65) Prior Publication Data

US 2019/0267847 A1    Aug. 29, 2019

Related U.S. Application Data

(63) Continuation of application No. PCT/JP2017/031397, filed on Aug. 31, 2017.

(30) Foreign Application Priority Data

Nov. 25, 2016    (JP) .............................. JP2016-228962

(51) Int. Cl.
| | |
|---|---|
| *H02J 50/20* | (2016.01) |
| *A61B 5/01* | (2006.01) |
| *A61B 5/1455* | (2006.01) |
| *A61B 5/18* | (2006.01) |
| *A61B 5/00* | (2006.01) |
| *B60W 50/14* | (2020.01) |
| *G08G 1/16* | (2006.01) |

(Continued)

(52) U.S. Cl.
CPC .............. *H02J 50/20* (2016.02); *A61B 5/002* (2013.01); *A61B 5/01* (2013.01); *A61B 5/14553* (2013.01);

(Continued)

(58) Field of Classification Search
CPC ........... H02J 50/00; A61B 5/00; B60W 40/00; B60W 50/00; B60W 2540/22; G08G 1/16; B60H 1/00
See application file for complete search history.

(56) References Cited

U.S. PATENT DOCUMENTS

| | | | |
|---|---|---|---|
| 2002/0017994 A1* | 2/2002 | Balkin ................... | G16H 15/00 340/573.1 |
| 2007/0222426 A1 | 9/2007 | Waffenschmidt et al. | |

(Continued)

FOREIGN PATENT DOCUMENTS

| | | |
|---|---|---|
| JP | 2000301963 A | 10/2000 |
| JP | 2007538478 A | 12/2007 |

(Continued)

*Primary Examiner* — Rexford N Barnie
*Assistant Examiner* — Joseph N Inge
(74) *Attorney, Agent, or Firm* — Harness, Dickey & Pierce, P.L.C.

(57) ABSTRACT

A wireless power supply system is provided to include a headset and a vehicle-side system. The headset, which is attached to a head of a driver of a vehicle, is configured (i) to generate an electric power by using a received electromagnetic wave, (ii) to actuate a sensor with the generated electric power to measure an activity of the driver, and (iii) to transmit activity measurement data indicating a measurement result. The vehicle-side system, which is provided to the vehicle, is configured (i) to transmit the electromagnetic wave, (ii) to receive the activity measurement data from the headset, and (iii) to monitor the activity of the driver based on the received measurement data. The transmitting or receiving state of the electromagnetic wave is monitored to provide a monitoring result, which is to be notified.

18 Claims, 14 Drawing Sheets

(51) Int. Cl.
  *B60W 40/08* (2012.01)
  *H02J 50/12* (2016.01)
  *H02J 50/80* (2016.01)
  *B60H 1/00* (2006.01)

(52) U.S. Cl.
  CPC .............. *A61B 5/18* (2013.01); *A61B 5/4809* (2013.01); *A61B 5/6803* (2013.01); *B60W 40/08* (2013.01); *B60W 50/14* (2013.01); *G08G 1/16* (2013.01); *H02J 50/12* (2016.02); *H02J 50/80* (2016.02); *A61B 5/6893* (2013.01); *A61B 2503/22* (2013.01); *A61B 2560/0214* (2013.01); *B60H 1/00735* (2013.01); *B60W 2540/22* (2013.01)

(56) References Cited

U.S. PATENT DOCUMENTS

| | | | | |
|---|---|---|---|---|
| 2009/0156907 A1* | 6/2009 | Jung | ................ | A61B 5/14553 600/300 |
| 2009/0157481 A1* | 6/2009 | Jung | ................ | G06Q 30/02 709/205 |
| 2009/0312998 A1* | 12/2009 | Berckmans | ............ | G16H 50/50 703/11 |
| 2014/0252813 A1* | 9/2014 | Lee | ................ | H02J 50/40 297/180.12 |
| 2015/0328985 A1* | 11/2015 | Kim | ................ | A61B 5/18 180/272 |
| 2015/0363979 A1 | 12/2015 | Takano et al. | | |
| 2017/0151959 A1* | 6/2017 | Boesen | ................ | A61B 5/6803 |
| 2017/0166054 A1* | 6/2017 | Ayala Rodriguez | ................ | A61B 5/6846 |
| 2017/0303842 A1* | 10/2017 | Yoshida | ............ | B60W 50/0097 |
| 2019/0046100 A1* | 2/2019 | Li | ................ | A61B 5/6803 |

FOREIGN PATENT DOCUMENTS

| | | |
|---|---|---|
| JP | 2009109319 A | 5/2009 |
| JP | 2012176294 A | 9/2012 |
| JP | 2014155207 A | 8/2014 |
| JP | 2015134515 A | 7/2015 |
| JP | 2015135513 A | 7/2015 |

* cited by examiner

FIG. 13

HEAD IS SHIFTED TO THE RIGHT.
PLEASE RETURN TO THE LEFT SLIGHTLY.

FIG. 14

POWER RECEPTION IS ABNORMAL.

WIRELESS POWER SUPPLY SYSTEM AND NON-TRANSITORY TANGIBLE COMPUTER-READABLE STORAGE MEDIUM

CROSS REFERENCE TO RELATED APPLICATIONS

The present application is a continuation application of International Patent Application No. PCT/JP2017/031397 filed on Aug. 31, 2017, which designated the United States and claims the benefit of priority from Japanese Patent Application No. 2016-228962 filed on Nov. 25, 2016. The entire disclosures of all of the above applications are incorporated herein by reference.

TECHNICAL FIELD

The present disclosure relates to a wireless power supply system and a non-transitory tangible computer-readable storage medium.

BACKGROUND

There is conventionally provided a system that monitors the state of a driver and performs warning and/or driving assistance when detecting the deterioration in the driving ability of the driver, and prevents the occurrence of traffic accidents. For example, a configuration is disclosed which detects, as a detected driver's activity, the line of sight of a driver with a sight line sensor and the rotation angle of the steering wheel with a rotation angle sensor to monitor the state of the driver.

According to an example of the present disclosure, a wireless power supply system is provided to include a headset and a vehicle-side system. The headset, which is attached to a head of a driver of a vehicle, is configured (i) to generate an electric power by using a received electromagnetic wave, (ii) to actuate a sensor with the generated electric power to measure an activity of the driver, and (iii) to transmit activity measurement data indicating a measurement result. The vehicle-side system, which is provided to the vehicle, is configured (i) to transmit the electromagnetic wave, (ii) to receive the activity measurement data from the headset, and (iii) to monitor the activity of the driver based on the received measurement data. The transmitting or receiving state of the electromagnetic wave is monitored to provide a monitoring result, which is to be notified.

BRIEF DESCRIPTION OF DRAWINGS

The above and other objects, features and advantages of the present disclosure will become more apparent from the following detailed description made with reference to the accompanying drawings.

FIG. 13 is a diagram (part 1) showing a notifying screen;

FIG. 14 is a diagram (part 2) showing a notifying screen; and

DETAILED DESCRIPTION

Figure 1:
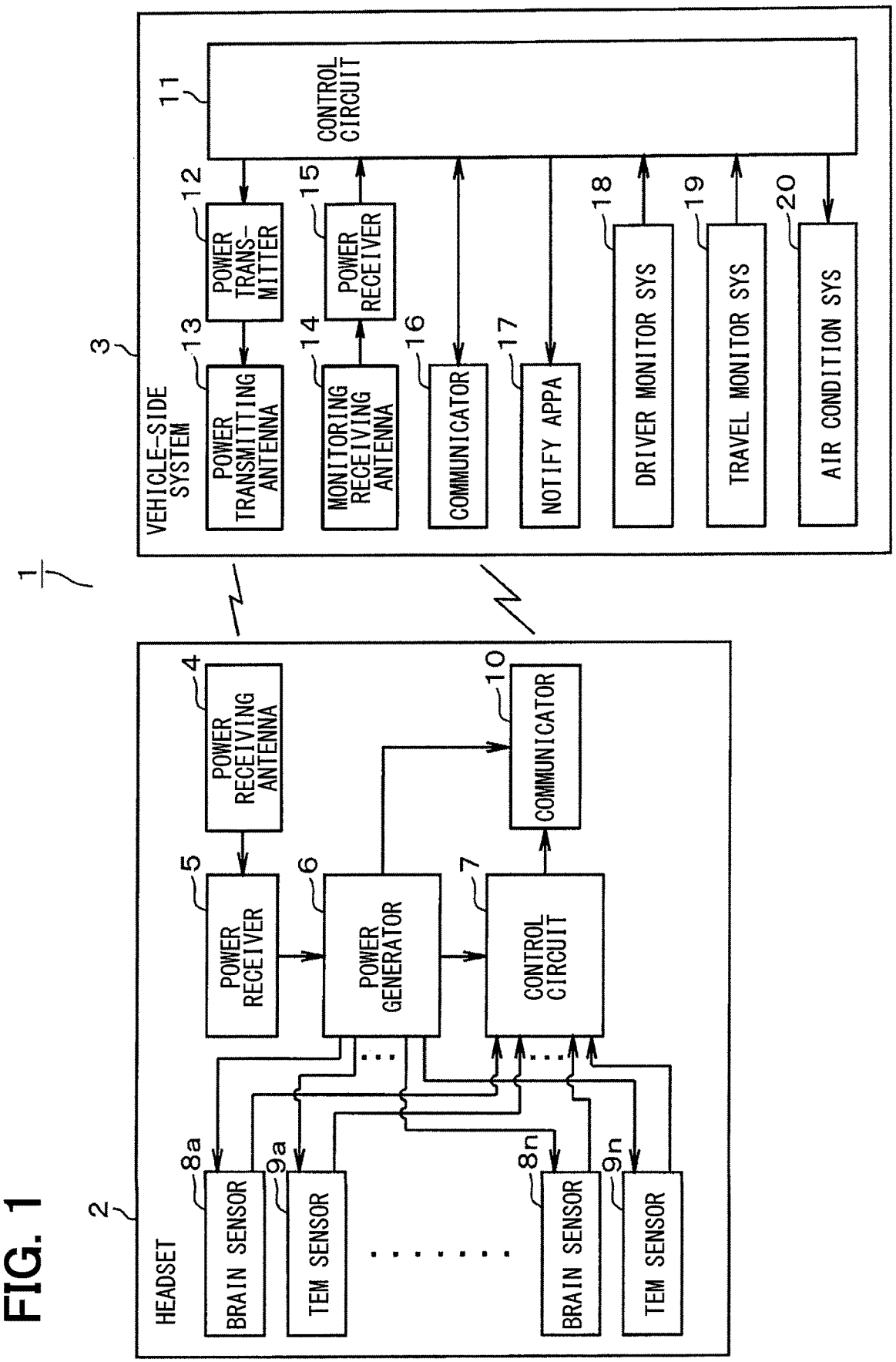
FIG. 1 is a functional block diagram showing an embodiment of the present disclosure.

The following will describe a wireless power supply system 1 mounted in a vehicle according to an embodiment of the present disclosure with reference to the drawings. The wireless power supply system 1 includes a headset 2 attached on the head of a driver of the vehicle and a vehicle-side system 3 mounted in the vehicle. The headset 2 includes a power receiving antenna 4, a power receiver 5, a power generator 6, a control circuit 7, a plurality of brain sensors 8a to 8n, a plurality of temperature sensors 9a to 9n, and a communicator 10.

The power receiving antenna 4 is, for example, a coil antenna including an annular coil, electromagnetically coupled to the power transmitting antenna of the vehicle-side system 3, and receives the electromagnetic wave transmitted from the power transmitting antenna. Note that the power receiving antenna 4 need not be a coil antenna, but may be a plane antenna or a chip antenna. Further, in order to increase the power receiving efficiency, the coil may be held by a material enabled to adjust permeability and/or dielectric constant.

The power receiver 5 includes a rectifying circuit to rectify an electromagnetic wave received by the power receiving antenna 4, generate a DC current, and output the generated DC current to the power generator 6. When receiving a DC current from the power receiver 5, the power generator 6 generates operating power from the input DC current and supplies the generated operating power to the control circuit 7, the plurality of brain sensors 8a to 8n, the plurality of temperature sensors 9a to 9n, and the communicator 10. The power generator 6 selectively supplies operating power to any one of the plurality of brain sensors 8a to 8n and the plurality of temperature sensors 9a to 9n; thereby, the plurality of brain sensors 8a to 8n and the plurality of temperature sensors 9a to 9n may be selectively actuated or driven in accordance with the drive signal. The power generator 6 also functions as a capacitor and also has a function of accumulating or storing the generated operating power. That is, by providing a capacitor having a relatively large storage capacity, the period of time during which the brain sensors 8a to 8n be driven in the non-powered state may be made relatively long.

The control circuit 7 controls the operation of the headset 2 when receiving the operating power from the power generator 6. As one of examples of the present embodiment, the control circuit 7 is configured by using a well-known microcomputer containing a CPU; a non-transitory tangible storage medium such as a ROM, a RAM; I/O interfaces; and a bus. The control circuit 7 (i.e., the microcomputer 7) executes a control program stored in the ROM to provide a plurality of functions for controlling the operation of the headset 2.

The brain sensors 8a to 8n are driven by receiving the operating power from the power generator 6, and measure the brain activity of the driver using the NIRS (Near Infra-Red Spectroscopy) technique. In the information processing of the brain, it is thought that the two systems (i.e., the signaling system played by neuronal activity and the energy supply system supporting nerve activity) are closely related. When nerve activity occurs, blood vessels around it expand and an adjustment mechanism works to supply a large amount of arterial blood including oxygen and glucose, which are energy sources. In tissues in the vicinity of the active nerve, it is assumed that the blood flow rate and the blood volume increase, and the oxidation state of blood (that is, the ratio of oxyhemoglobin concentration to deoxyhemoglobin concentration) changes. The relationship between such neural activity and cerebral blood reaction is called neurovascular coupling; in the NIRS technique, local hemoglobin concentration in the brain is detected based on the assumption that neurovascular coupling exists, to measure the brain activity of a person.

Specifically, each of the brain sensors $8a$ to $8n$ includes a radiator that radiates near-infrared light on the scalp of the driver and a light receiver that receives diffusedly reflected light of near-infrared light radiated from the radiator. When near-infrared light is radiated onto the scalp of the driver from the radiator, the light component of the near-infrared light diffuses into the brain tissue due to high bio-permeability that permeates the skin and bone, thereby reaching the cerebral cortex deep in about 20-30 mm. Then, due to the property that the oxyhemoglobin concentration and the deoxyhemoglobin concentration in the blood have different optical absorption characteristics, the light component diffusely reflected at a position several cm away from the irradiated point is detected by the light receiver. In this manner, the brain sensors $8a$ to $8n$ detect the light component, estimate changes in oxyhemoglobin concentration and deoxyhemoglobin concentration in the cerebral cortex, and measure the brain activity of the driver. The brain sensors $8a$ to $8n$ may estimate the change in the total hemoglobin concentration, which is the aggregate of both the oxyhemoglobin concentration and deoxyhemoglobin concentration of the cerebral cortex, as well as the brain activity of the driver. Then, the brain sensors $8a$ to $8n$ output brain activity measurement data indicating the measurement result to the control circuit 7.

The temperature sensors $9a$ to $9n$ are provided to correspond to the brain sensors $8a$ to $8n$, measure the temperatures of the brain sensors $8a$ to $8n$, and output temperature measurement data indicating the measured results to the control circuit 7. Incidentally, one temperature sensor may be provided for all of the plurality of brain sensors $8a$ to $8n$. When receiving the brain activity measurement data from the brain sensors $8a$ to $8n$ and receiving the temperature measurement data from the temperature sensors $9a$ to $9n$, the control circuit 7 transmits a sensor signal including the received brain activity measurement data and temperature measurement data via the communicator 10 to the vehicle-side system 3 by wireless communication. Further, the control circuit 7 transmits the reception intensity signal including the reception intensity of the electromagnetic wave in the power receiving antenna 4 to the vehicle-side system 3 via the communicator 10 by wireless communication.

The vehicle-side system 3 includes a control circuit 11, a power transmitter 12, a power transmitting antenna 13, a monitoring power receiving antenna 14, a monitoring power receiver 15, a communicator 16, a notification apparatus 17, a driver monitoring system 18, a vehicle travel monitoring system 19, and an air conditioning system 20.

The control circuit 11 controls the operation of the vehicle-side system 3. The power transmitter 12 transmits electromagnetic waves from the power transmitting antenna 13. The power transmitting antenna 13, which is fixedly provided in the passenger compartment, is a coil antenna composed of an annular coil, for instance; the power transmitting antenna 13 is electromagnetically coupled with the power receiving antenna 4 of the above-described headset 2, thereby transmitting the electromagnetic waves to the power receiving antenna 4. Note that the power transmitting antenna 13 need not be a coil antenna but may be a planar antenna or a chip antenna. Further, in order to increase the power transmission efficiency, the coil may be held by a material enabled to adjust permeability and/or dielectric constant.

The monitoring power receiving antenna 14, which is fixedly provided in the vicinity of the power transmitting antenna 13 in the passenger compartment, is a coil antenna composed of an annular coil, for instance; the monitoring power receiving antenna 14 is electromagnetically coupled with the above power transmitting antenna 13, thereby receiving electromagnetic wave transmitted from the power transmitting antenna 13. Note that the monitoring power receiving antenna 14 need not necessarily be a coil antenna but may be a planar antenna or a chip antenna. Further, in order to increase the power receiving efficiency, the coil may be held by a material enabled to adjust permeability and/or dielectric constant.

The monitoring power receiver 15, which includes a rectifying circuit, rectifies the electromagnetic wave received by the monitoring power receiving antenna 14, generates a DC current, and outputs the generated DC current to the control circuit 11. Upon receiving the sensor signal from the headset 2, the communicator 16 outputs the received sensor signal to the control circuit 11.

The notification apparatus 17 includes a display and a speaker, for instance; when receiving a notification command signal from the control circuit 11, the notification apparatus 17 performs a notifying operation according to the received notification command signal. The driver monitoring system 18 is a system including a camera or the like for photographing the face of the driver, monitors the state of the driver, and outputs a monitoring signal including the monitoring result to the control circuit 11. The vehicle travel monitoring system 19 is a system for detecting acceleration control accompanying accelerator operation, deceleration control accompanying brake operation, steering control accompanying steering operation, monitors the state of vehicle travel, and outputs a monitoring signal including the monitoring result to the control circuit 11. When receiving the air conditioning control signal from the control circuit 11, the air conditioning system 20 performs air conditioning control in the passenger compartment according to the received air conditioning control signal.

Figure 2:
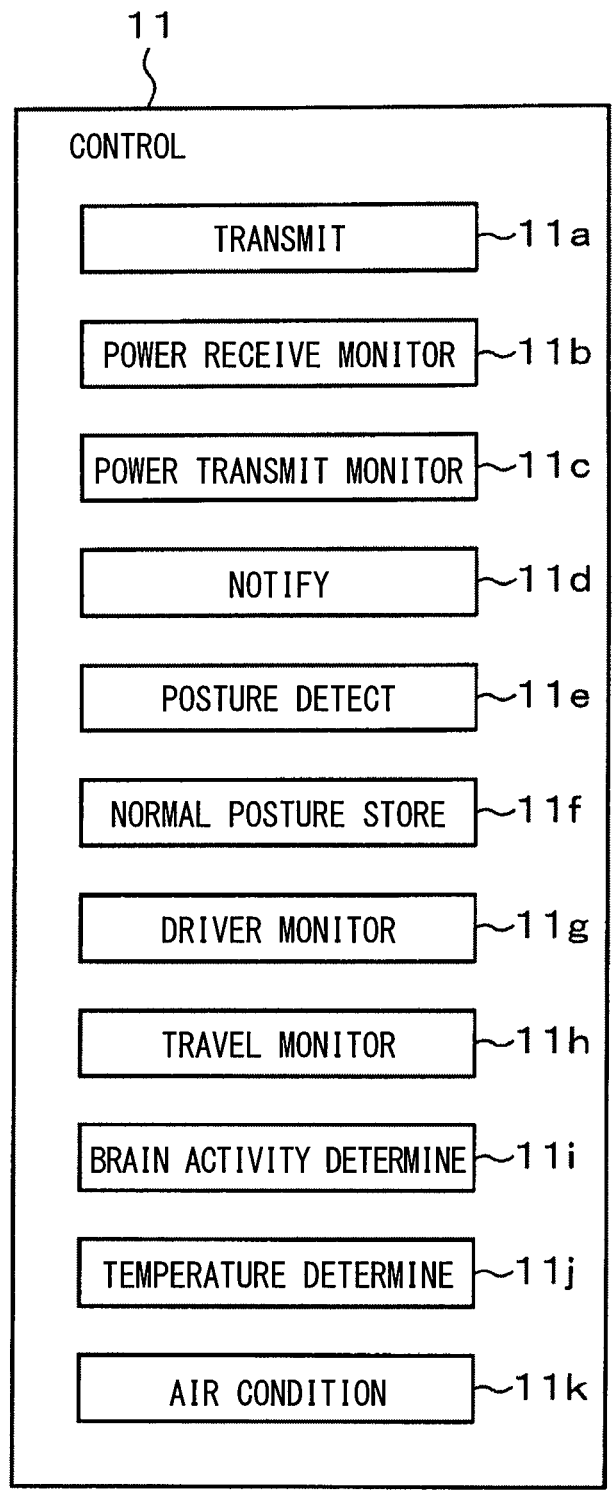
FIG. 2 is a diagram showing functions of a microcomputer.

As shown in FIG. 2, the control circuit 11 includes a plurality of sections as follows: a transmission control section 11*a*, a power reception monitoring section 11*b*, a power transmission monitoring section 11*c*, a notification control section 11*d*, a posture detection section 11*e*, a normal posture storage section 11*f*, a driver monitoring section 11*g*, a vehicle travel monitoring section 11*h*, a brain activity determination section 11*i*, a temperature determination section 11*j*, and an air conditioning control section 11*k*, to achieve respective functions.

As one of examples of the present embodiment, in the present embodiment, each of these sections 11*a* to 11*k* is configured by the control circuit 11 executing a control program stored in a storage in a software manner. That is, the control circuit 11 is configured by using a well-known microcomputer containing a CPU; a non-transitory tangible storage medium such as a ROM, a RAM; I/O interfaces; and a bus. The control circuit 11 (i.e., the microcomputer 11) executes a control program (e.g., a power transmission and reception monitoring program) stored in the ROM to provide a plurality of functions by using the sections.

The transmission control section 11a controls transmission of electromagnetic waves from the power transmitting antenna 13. When the reception intensity signal transmitted from the headset 2 is received by the communicator 16, the power reception monitoring section 11b acquires and determines the reception intensity of the electromagnetic wave in the power receiving antenna 4, and monitors the receiving state of the electromagnetic wave by the power receiving antenna 4. That is, the power transmitting antenna 13 is fixedly provided in the passenger compartment and the power receiving antenna 4 is provided in the headset 2. When the driver wearing the headset 2 moves their head, the relative position between the power transmitting antenna 13 and the power receiving antenna 4 thus changes while the reception intensity of the electromagnetic wave in the power receiving antenna 4 thus changes. When the reception intensity of the electromagnetic wave in the power receiving antenna 4 is equal to or lower than a predetermined intensity for a predetermined period of time, the power reception monitoring section 11b determines that the receiving state of the electromagnetic wave by the power receiving antenna 4 is unstable.

The power transmission monitoring section 11c acquires and determines the reception intensity of electromagnetic waves in the monitoring power receiving antenna 14 and monitors the transmitting state of electromagnetic waves from the power transmitting antenna 13. That is, both the power transmitting antenna 13 and the monitoring power receiving antenna 14 are fixedly provided in the passenger compartment; as long as the transmission intensity of the electromagnetic wave from the power transmitting antenna 13 does not change, the reception intensity of the electromagnetic wave at the monitoring power receiving antenna 14 is constant. When the transmission intensity of the electromagnetic wave from the power transmitting antenna 13 changes, the reception intensity of the electromagnetic wave in the monitoring power receiving antenna 14 thus changes. The power transmission monitoring section 11c determines that the transmission state of the electromagnetic wave from the power transmitting antenna 13 is unstable when a state in which the reception intensity of the electromagnetic wave in the monitoring power receiving antenna 14 is equal to or less than a predetermined intensity continues for a predetermined period of time.

Upon receiving a notification command signal, the notification control section 11d notifies (i) the monitoring result of the power reception monitoring section 11b and/or (ii) the monitoring result of the power transmission monitoring section 11c, from the notification apparatus 17 according to the received notification command signal. That is, when determining that the receiving state of the electromagnetic wave by the power receiving antenna 4 or the transmitting state of the electromagnetic wave from the power transmitting antenna 13 is unstable, the notification control section 11d notifies the fact from the notification apparatus 17 by displaying images or announcing speeches.

The posture detection section 11e detects the posture of the driver. The normal posture storage section 11f stores in a storage, as a normal posture, the posture of the driver when the power reception monitoring section 11b determines that the receiving state of the electromagnetic wave is stable. When the power reception monitoring section 11b determines that the receiving state of the electromagnetic wave is unstable, the notification control section 11d notifies the notification information prompting to return the current posture to the normal posture. That is, for example, suppose cases that the current posture of the driver is inclined to the right from the normal posture and the receiving state of the electromagnetic wave is unstable due to the inappropriate position of the power receiving antenna 4 with respect to the power transmitting antenna 13. In such cases, the notification control section 11d notifies the notification information prompting to return the current posture to the normal posture.

The driver monitoring section 11g monitors the state of the driver using the monitoring signal input from the driver monitoring system 18. The driver monitoring section 11g monitors whether or not the state of the driver is in a normal state in which safe driving may be maintained, for example, from a change in the pupil of the driver or the sight line direction of the driver. The driver monitoring section 11g creates a database by digitizing changes in the pupil of the driver and the sight line direction, for example, when the driver is in a normal state. When the numerical values such as changes in the pupil of the driver and the sight line direction deviate from the numerical values in the database, it is determined that the state or condition of the driver is abnormal.

The vehicle travel monitoring section 11h uses the monitoring signal input from the vehicle travel monitoring system 19 to monitor the state of vehicle travel. The vehicle travel monitoring section 11h monitors whether or not the travel state of vehicle is in a normal state where safe driving can be maintained, for example, from the changes in acceleration control, deceleration control, steering control, or the like. For example, the vehicle travel monitoring section 11h creates a database by digitalizing the changes in the acceleration control, the deceleration control, the steering control, etc. in the normal state. When numerical values of the changes in the acceleration control, deceleration control, steering control, etc. deviate from the numerical values in the database, it is determined that the travel state of the vehicle is abnormal.

When the sensor signal transmitted from the headset 2 is received by the communicator 16, the brain activity determination section 11i determines whether the brain activity of the driver is normal or abnormal based on the brain activity measurement data included in the sensor signal. When determining the abnormality of the brain activity of the driver, the brain activity determination section 11i performs a process for the abnormality of the brain activity. For example, when determining that the driver is in a non-awake state, the brain activity determination section 11i performs a process to awaken the driver such as giving a stimulus to the driver as a process for the abnormality of the brain activity. A method for giving a stimulus to the driver includes, for example, changing the transmission output of the electromagnetic wave from the power transmitting antenna 13 to change the intensity of the near infrared light radiated on the scalp of the driver from the brain sensors 8a to 8n.

When the sensor signal transmitted from the headset 2 is received by the communicator 16, the temperature determination section 11j determines the presence or absence of the abnormality of the temperature of the brain sensors 8a to 8n based on the temperature measurement data included in the sensor signal. When determining the presence of the abnormality, the temperature determination section 11*j* performs a process for the abnormality of the temperature. For example, when determining that the temperatures of the brain sensors 8*a* to 8*n* each have reached a predetermined temperature, the temperature determination section 11*j* controls the air conditioning system 20 by using the air conditioning control section 11*k* as a process for the abnormality of the temperature to allow the temperature to be less than the predetermined temperature.

Figure 3:
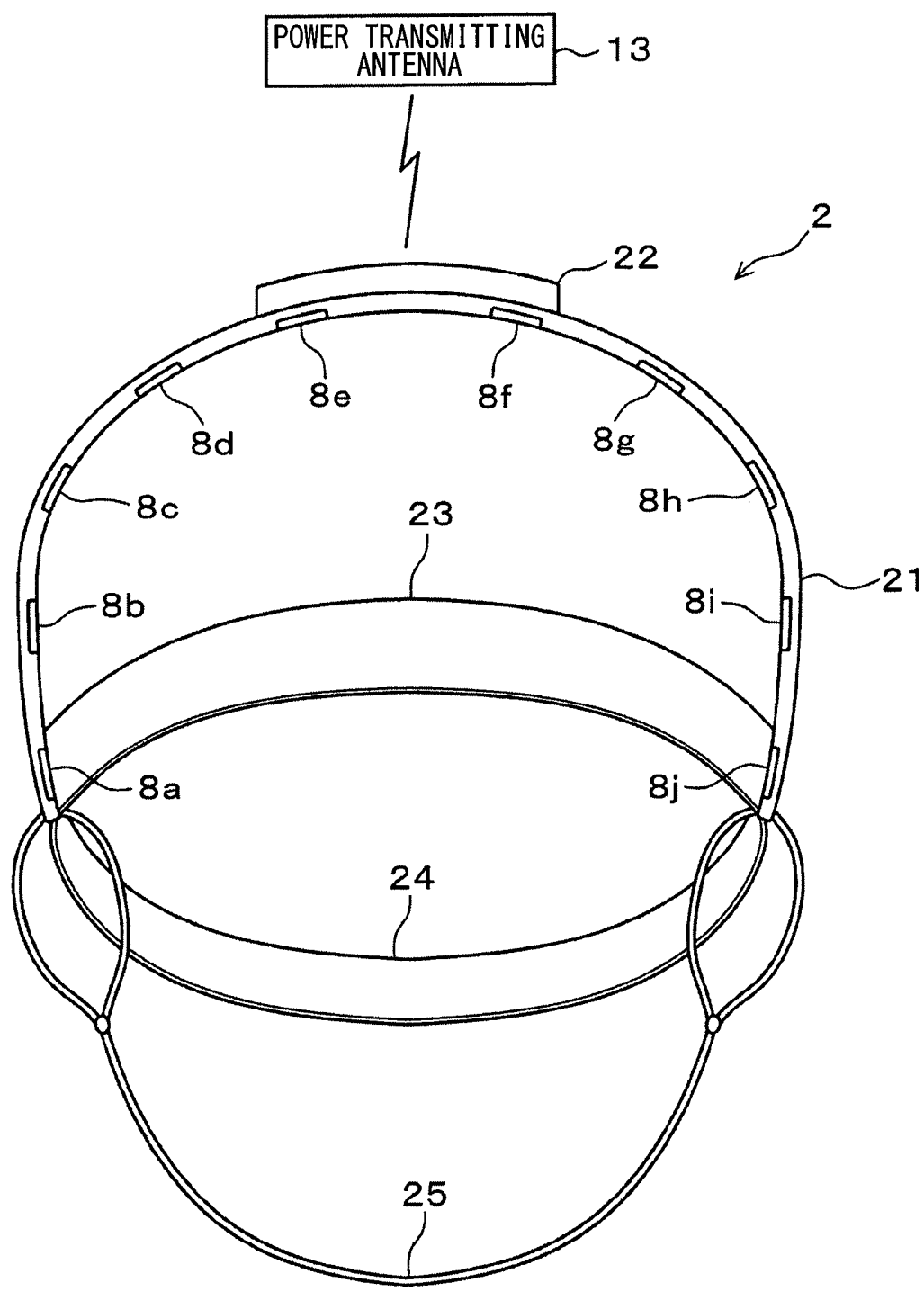
FIG. 3 is a diagram (part 1) showing a configuration of a headset.

The following will describe a mechanical configuration of the headset 2. The headset 2 includes (i) a type that receives electromagnetic waves from the above and (ii) a type that receives electromagnetic waves from the side. As shown in FIG. 3, the headset 2 for receiving electromagnetic waves from the above includes a controller box 22 attached to the upper portion of a curved main body 21 along the shape of a human head. The main body 21 is made of a flexible material and is deformable according to the shape of a human head. The main body 21 functions as a sensor holder which holds the brain sensors 8*a* to 8*n*. On the inner surface of the main body 21 contacting the scalp of a person, a plurality of brain sensors 8*a* to 8*n* are embedded in substantially the same intervals as shown in FIG. 3. Though not shown in FIG. 3, a plurality of temperature sensors 9*a* to 9*n* are also disposed at substantially equal intervals corresponding to a plurality of brain sensors 8*a* to 8*n*.

The controller box 22 includes or incorporates the above-described power receiving antenna 4, the power receiver 5, the power generator 6, the control circuit 7, and the communicator 10. The brain sensors 8*a* to 8*n* and the temperature sensors 9*a* to 9*n*, which are individually connected to the controller box 22 with power supply lines and signal lines (not shown), receive the operating power supplied from the power generator 6 via the power supply lines, and output the brain activity measurement data and temperature measurement data to the control circuit 7 via the signal lines. The main body 21 is integrally provided with a front holding portion 23 for holding the front side of the human head and a rear holding portion 24 for holding the rear side of the human head. The front holding portion 23 and the rear holding portion 24 are each made of a flexible material to be deformed according to the shape of the human head. The main body 21 is integrally provided with a jaw string 25 as an attachment assisting tool for hooking on the ear or neck so that the main body 21 is not detached from the head due to impact or the like.

Figure 4:
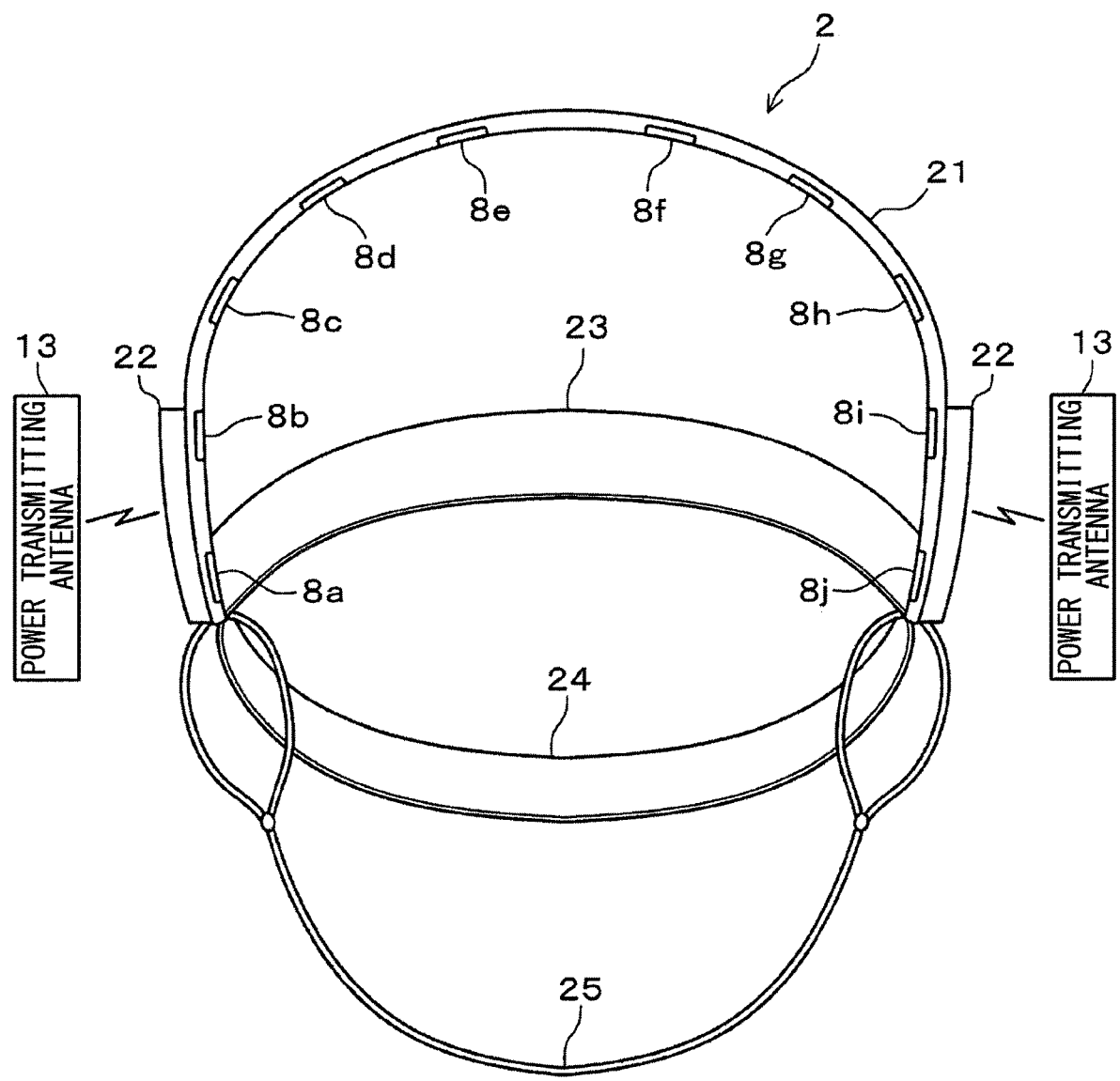
FIG. 4 is a diagram (part 2) showing a configuration of a headset.

As shown in FIG. 4, the headset 2 of a type receiving electromagnetic waves from the side is different from that of a type receiving the electromagnetic waves from the above in that two controller boxes 22 are provided to be attached to the left and right side portions of the main body 21; the other configuration is almost the same.

Figure 5:
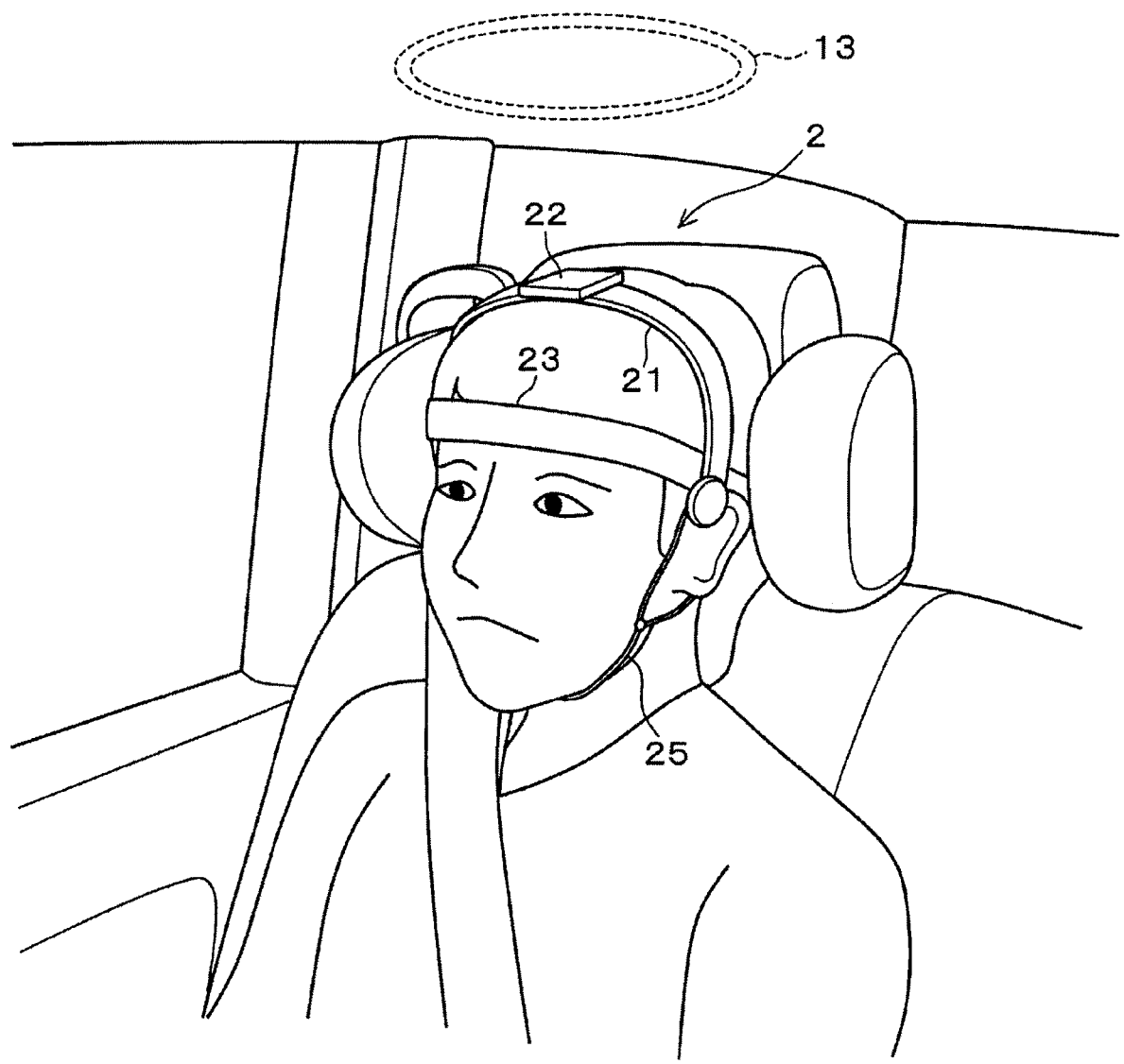
FIG. 5 is a diagram (part 1) showing a configuration in which a driver wearing a headset is seated in a driver's seat.
Figure 6:
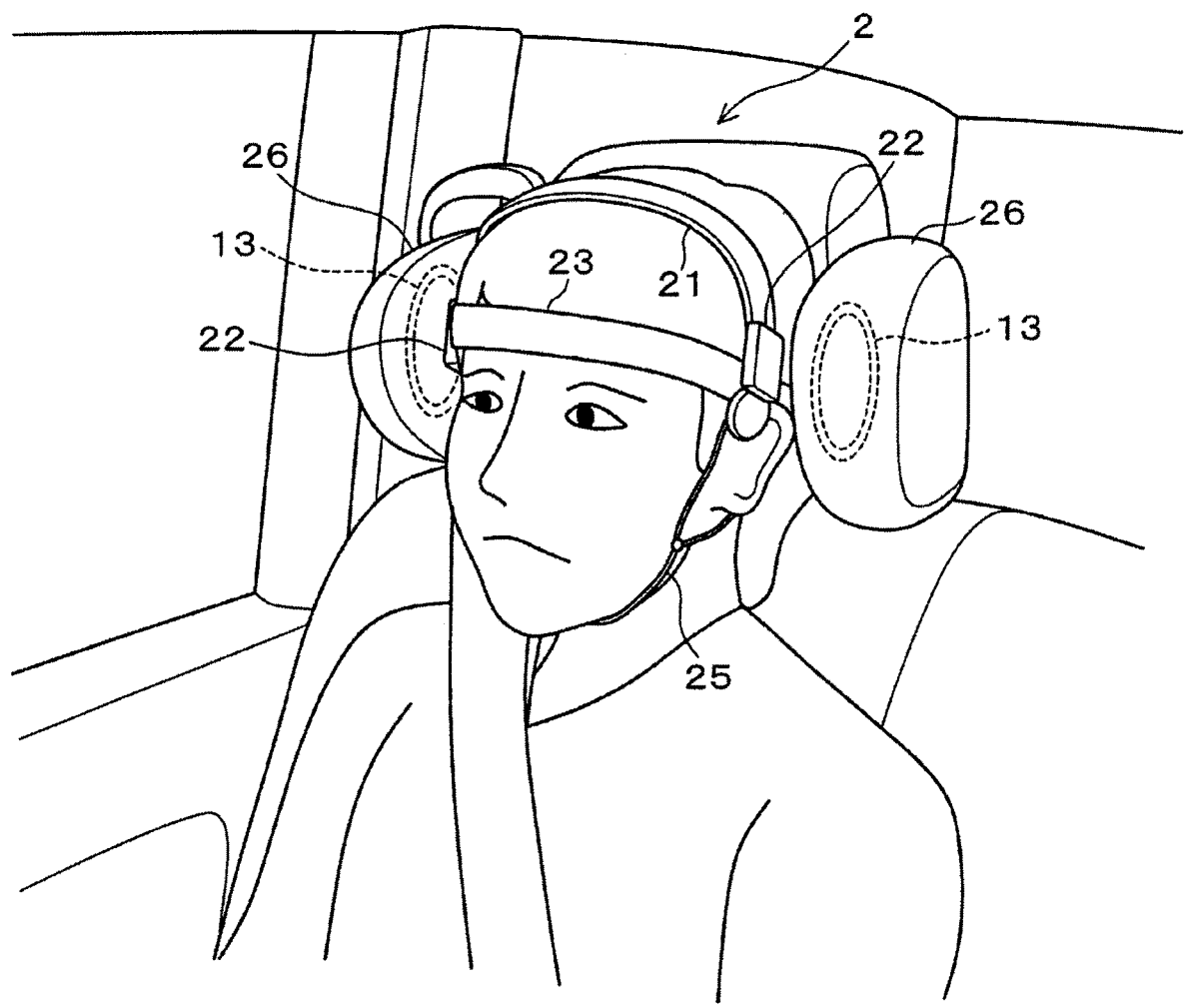
FIG. 6 is a diagram (part 2) showing a configuration in which a driver wearing a headset is seated in a driver's seat.

When the driver wearing the headset 2 of the type that receives the electromagnetic waves from the above is seated in the driver's seat, as shown in FIG. 5, the power receiving antenna 4 is located to be close to the power transmitting antenna 13 embedded in the ceiling of the vehicle interior of the vehicle. When the power receiving antenna 4 is located to be close to the power transmitting antenna 13, the power receiving antenna 4 receives the electromagnetic wave transmitted from the power transmitting antenna 13, to be supplied with the power from the above. When the driver wearing the headset 2 of the type that receives the electromagnetic waves from the side is seated in the driver's seat, the power receiving antenna 4 is located to be close to the power transmitting antenna 13 embedded in the head-rest 26 of the driver's seat, with respect to each of the right side and the left side of the driver or the main body 21, as shown in FIG. 6. When the power receiving antenna 4 is located to be close to the power transmitting antenna 13, the power receiving antenna 4 receives the electromagnetic wave transmitted from the power transmitting antenna 13, to be supplied with the power from the side. The above describes the headset 2 of a type that receives electromagnetic waves from the side including two controller boxes 22 attached to the left and right side portions of the main body 21. The controller box 22 may alternatively be attached to only one of the left side and the right side of the main body 21. Further, three controller boxes 22 may be attached to the upper portion and the left and right side portions of the main body 21.

Figure 7:
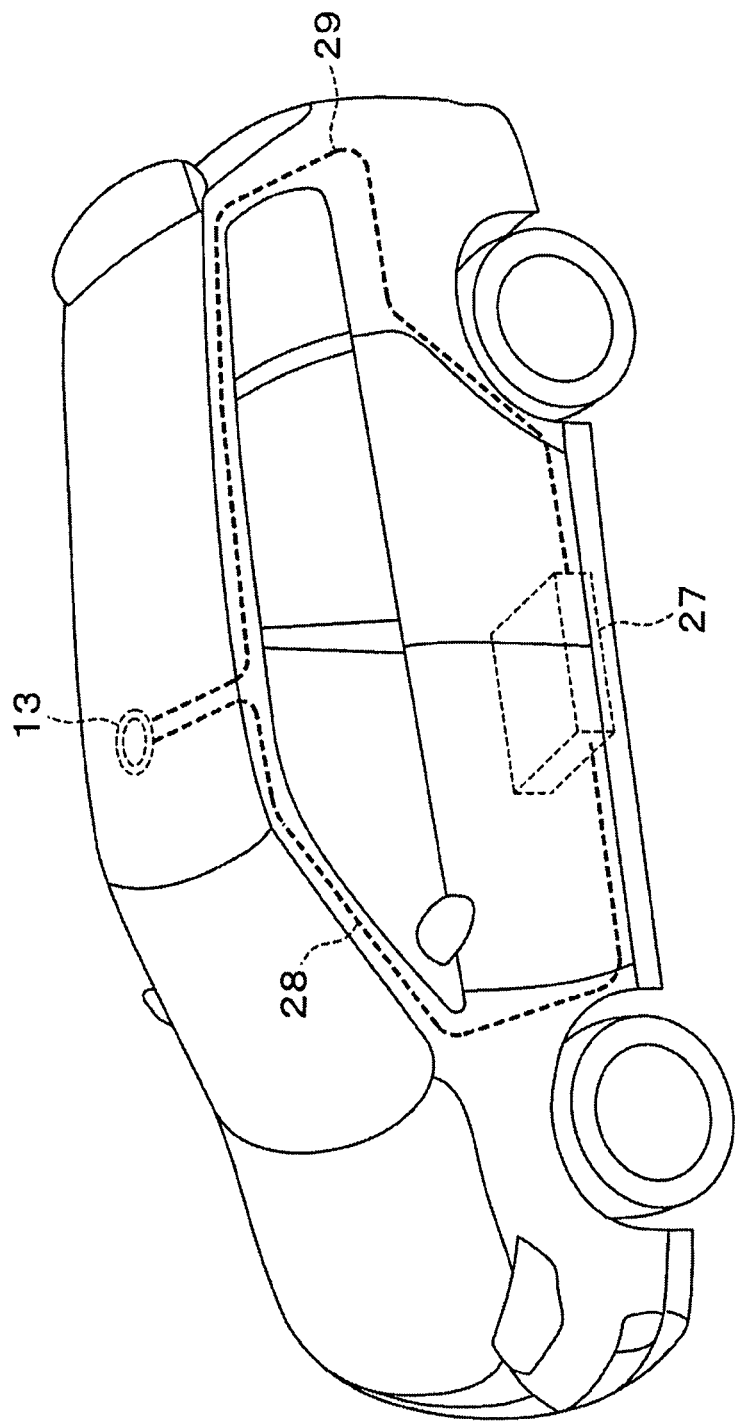
FIG. 7 is a diagram showing a configuration of a vehicle-side system.
Figure 8:
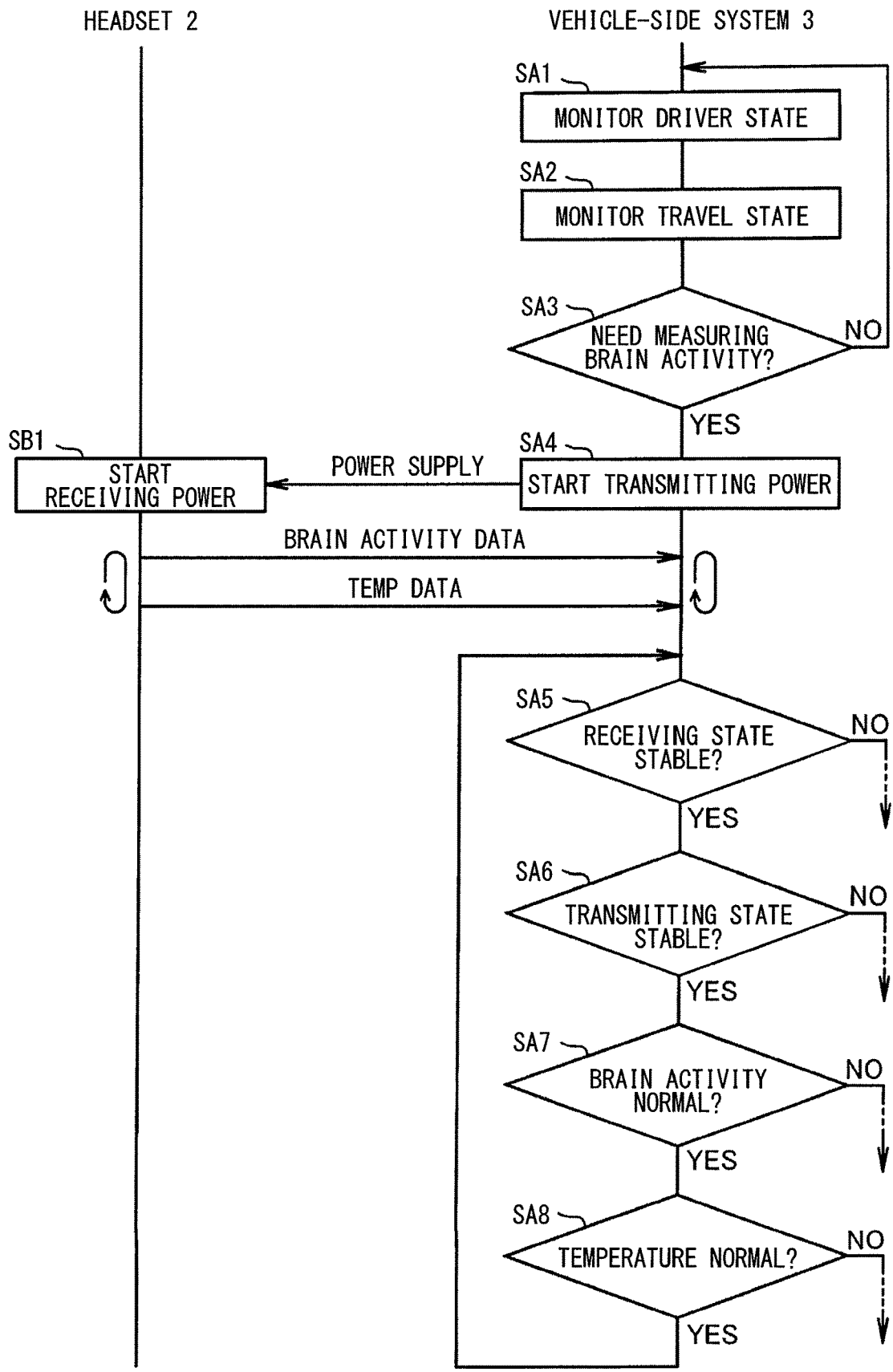
FIG. 8 is a sequence diagram (part 1)

The following will describe a mechanical configuration of the vehicle-side system 3. As shown in FIG. 7, in the vehicle-side system 3, the power is supplied from a battery 27 mounted on the vehicle to the power transmitting antenna 13 via two power supply lines 28, 29. That is, the power is supplied to the power transmitting antenna 13 from the battery 27 via the front power supply line 28 attached to the front of the vehicle, and the power is supplied to the power transmitting antenna 13 via the rear power supply line 29 attached to the rear of the vehicle from the battery 27. Even if either one of the front side of the vehicle and the rear side of the vehicle is damaged due to a vehicle accident or the like to damage one of the front power supply line 28 and the rear power supply line 29, the power supply via the other is secured to increase redundancy. FIG. 7 illustrates a configuration in which the power is supplied to the power transmitting antenna 13 arranged on the ceiling of the passenger compartment of the vehicle. The power transmitting antenna 13 embedded in the head-rest 26 in the passenger compartment may be supplied with power via the two power supply lines 28, 29.

The following will describe operations or sequence including sections (expressed as S), with reference to FIGS. 8 to 15. In the vehicle-side system 3, the operations or sequence may be mainly controlled by the control circuit 11; in the headset 2, the operations or sequence may be mainly controlled by the control circuit 7. In the vehicle-side system 3, the control circuit 11 uses the monitoring signal input from the driver monitoring system 18 to monitor the state of the driver (SA1). For example, suppose cases that the change in the pupil or the sight line direction of the driver is stable so that the driver is in a normal state enabled to maintain safe driving. In such cases, the control circuit 11 determines that it is not necessary to measure the brain activity (SA3: NO); then, monitoring of the state of the driver is continued. The control circuit 11 uses the monitoring signal input from the vehicle travel monitoring system 19 to monitor the state of vehicle travel (SA2). For example, suppose cases that the change in the acceleration control, the deceleration control, or the steering control is stable so that the vehicle travel is in a normal state enabled to maintain safe driving. In such cases, the control circuit 11 determines that it is not necessary to measure the brain activity (SA3: NO); then, monitoring of the state of the vehicle travel is continued.

On the other hand, suppose cases that the driver is in an abnormal state, such as frequent inattentiveness of the driver, disabled to maintain safe driving, or that the vehicle travel is in an abnormal state, such as a high frequency of rapid acceleration or sudden deceleration, disabled to maintain safe driving. In such cases, the control circuit 11 determines that it is necessary to measure the brain activity (SA3: YES); then, transmission of electromagnetic waves from the power transmitting antenna 13 is started (SA4).

The headset 2 (i.e., the control circuit 7) starts the reception of the electromagnetic wave transmitted from the power transmitting antenna 13, by using the power receiving antenna 4 (SB1). The received electromagnetic wave is rectified to generate a direct current; operating electric power is generated from the generated direct current; and the generated operating electric power is supplied to the control circuit 7, a plurality of brain sensors 8a to 8n, a plurality of temperature sensors 9a to 9n, and the communicator 10. In response to that the operating electric power is generated, the headset 2 is activated to transmit a sensor signal including the brain activity measurement data from the brain sensors 8a to 8n and the temperature measurement data from the temperature sensors 9a to 9n to the vehicle-side system 3.

In the vehicle-side system 3, upon receiving the sensor signal and the reception intensity signal from the headset 2, the control circuit 11 performs the following: determining whether the receiving state of the electromagnetic wave by the power receiving antenna 4 is stable (SA5, power transmission monitoring procedure); determining whether the transmitting state of the electromagnetic wave from the power transmitting antenna 13 is stable (SA6, power transmission monitoring procedure); determining whether the driver's brain activity is normal (SA7); and determining whether the temperatures of the brain sensors 8a to 8n are normal (SA8).

Figure 9:
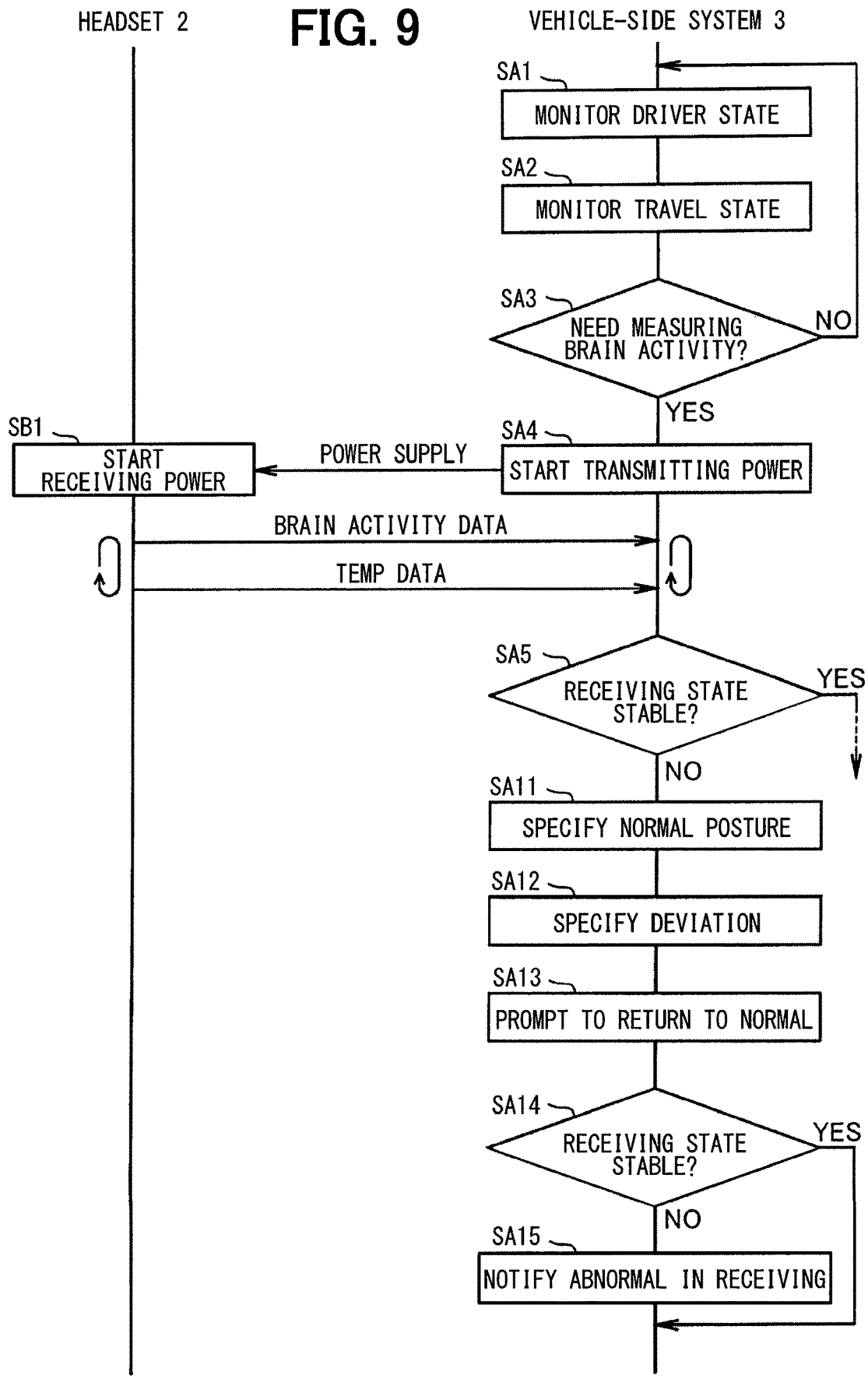
FIG. 9 is a sequence diagram (part 2)

Here, with reference to FIG. 9, suppose a case where the position of the head of the driver wearing the headset 2 changes; the reception intensity of the electromagnetic wave in the power receiving antenna 4 changes; and the state where the reception intensity of the electromagnetic wave in the power receiving antenna 4 is lower than a predetermined intensity continues for a predetermined period of time. In such a case, the control circuit 11 determines that the receiving state of the electromagnetic wave by the power receiving antenna 4 has become unstable (SA5: NO).

When determining that the receiving state of the electromagnetic wave by the power receiving antenna 4 becomes unstable, the control circuit 11 specifies the normal posture which is a posture of the driver when the receiving state of the electromagnetic wave is stable (SA11), and specifies the deviation between the current posture of the driver and the normal posture (SA12). Upon specifying the deviation, the control circuit 11 outputs a notification command signal to the notification apparatus 17 and notifies the notification information prompting to return the current posture to the normal posture (SA13, notification control procedure). For example, if the posture of the driver is inclined to the right side from the normal posture, the control circuit 11 displays a message such as "Head is shifted to the right. Please return to the left slightly" on the display or the notifying screen, as shown in FIG. 13, to notify the driver of the notification information prompting to return the current posture to the normal posture. As a result, the driver can grasp that their head is shifted to the right, and move it a little to the left to respond appropriately.

The control circuit 11 again determines whether the electromagnetic wave receiving state by the power receiving antenna 4 is stable (SA14). When determining that the receiving state of the electromagnetic wave by the power receiving antenna 4 is unstable (i.e., determines that it has not returned from the unstable state to the stable state (SA14: NO), the control circuit 11 outputs the notification command signal indicating that the reception is abnormal from the notification apparatus 17 (SA15, notification control procedure). As shown in FIG. 14, the control circuit 11 displays a message such as "Power reception is abnormal" on the display or notifying screen and notifies the driver of the notification information indicating that the power reception is abnormal. Thus, the driver can grasp that the power reception is abnormal.

Figure 10:
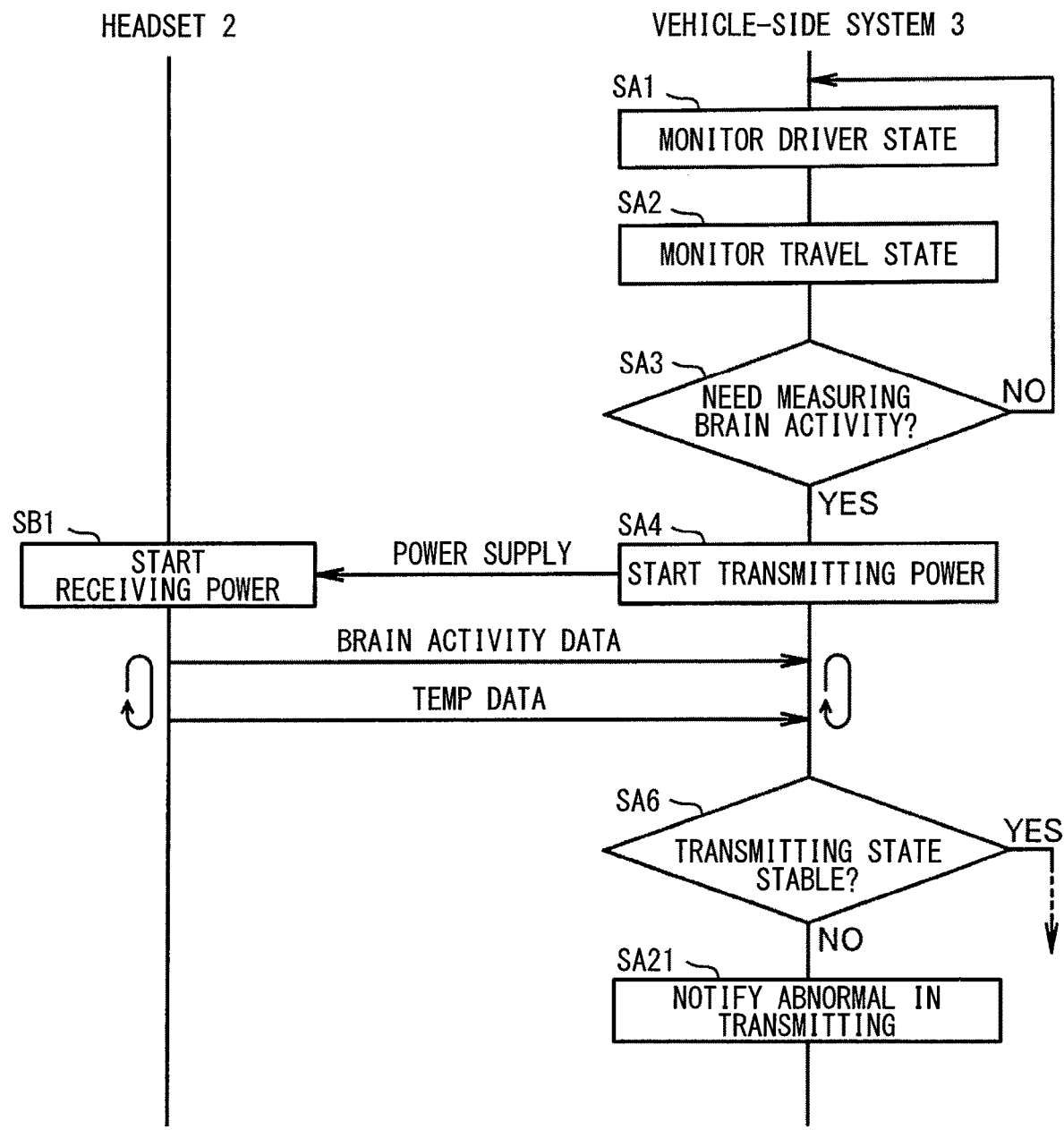
FIG. 10 is a sequence diagram (part 3)
Figure 15:
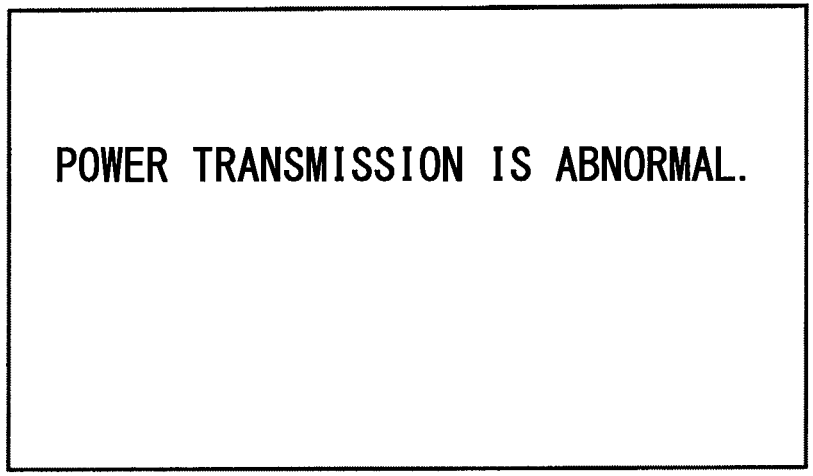
FIG. 15 is a diagram (part 3) showing a notifying screen.

Also, with reference to FIG. 10, suppose a case that the reception intensity of the electromagnetic wave in the monitoring power receiving antenna 14 changes; and the state in which the reception intensity of the electromagnetic wave in the monitoring power receiving antenna 14 is equal to or less than a predetermined intensity continues for a predetermined period of time. In such a case, the control circuit 11 determines that the transmitting state of the electromagnetic wave from the power transmitting antenna 13 has become unstable (SA6: NO). When determining that the transmitting state of the electromagnetic wave from the power transmitting antenna 13 has become unstable, the control circuit 11 outputs a notification command signal from the notification apparatus 17 so as to notify the notification information indicating that the power transmission is abnormal (SA21, notification control procedure). As shown in FIG. 15, the control circuit 11 displays a message such as "transmission is abnormal", as shown in FIG. 15, on the display or notifying screen and notifies the notification information indicating that the power transmission is abnormal. Thus, the driver can grasp that the power transmission is abnormal.

Figure 11:
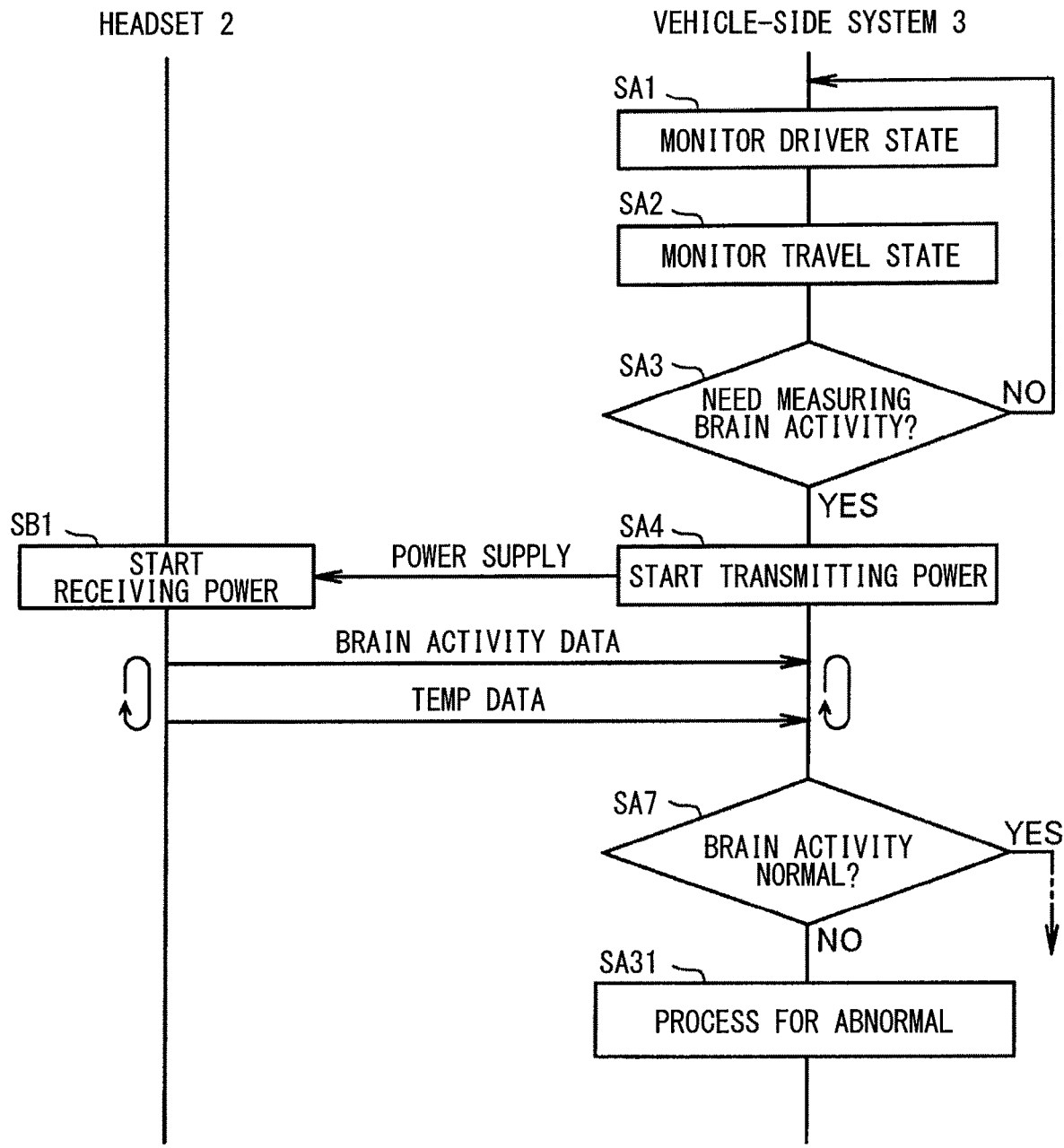
FIG. 11 is a sequence diagram (part 4)

Also, as shown in FIG. 11, when determining that the brain activity of the driver is abnormal (SA7: NO), the control circuit 11 performs a process for the abnormality of the brain activity (SA31). For example, when determining that the driver is in a non-awake state, the control circuit 11 performs a process of awakening the driver such as giving a stimulus to the driver as a process for the abnormality of the brain activity.

Figure 12:
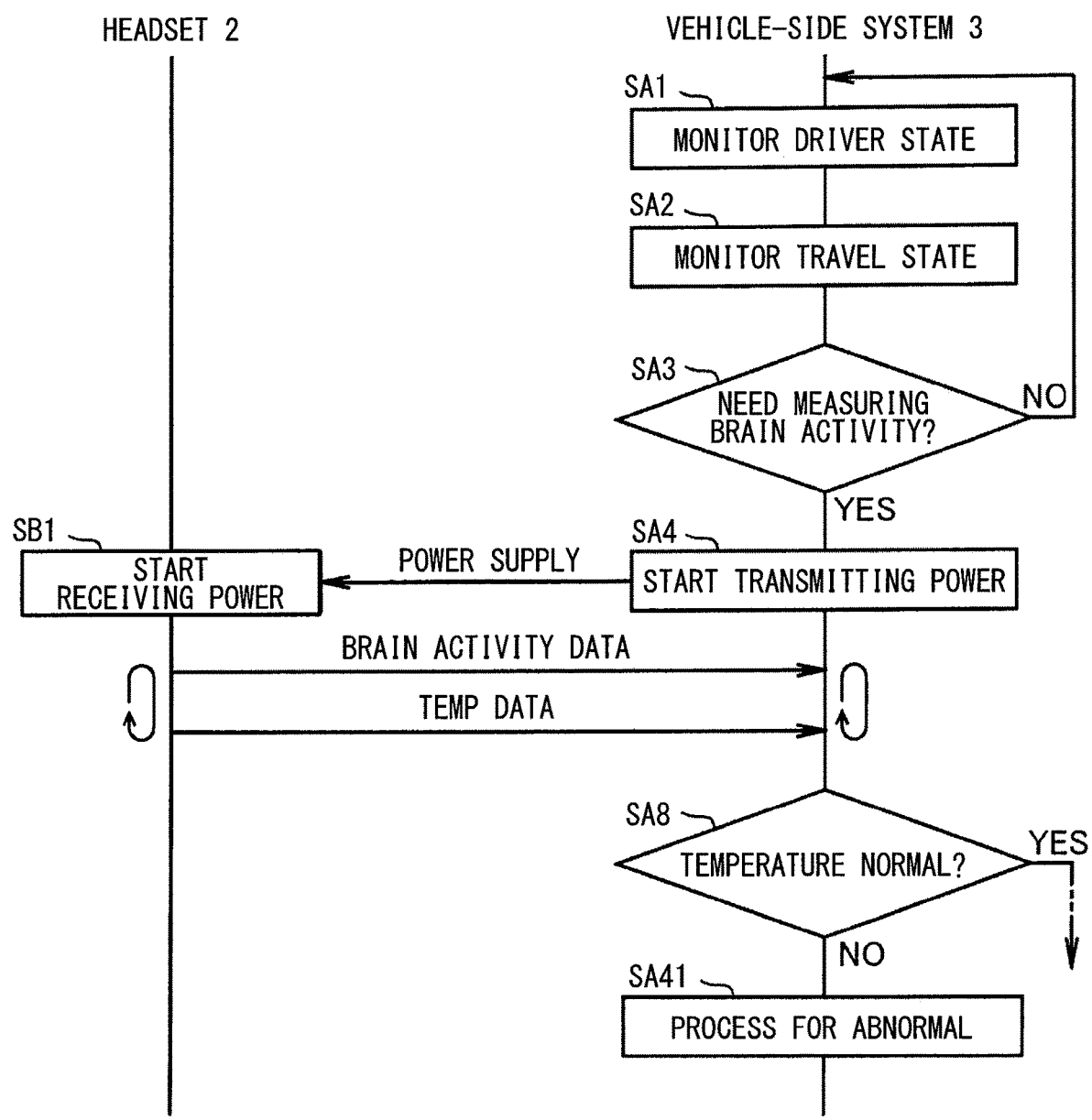
FIG. 12 is a sequence diagram (part 5)

Further, as shown in FIG. 12, when determining that the temperatures of the brain sensors 8a to 8n are abnormal (SA8: NO), the control circuit 11 performs a process for abnormality in temperature of the brain sensors 8a to 8n (SA41). Upon determining that the temperatures of the brain sensors 8a to 8n have reached a predetermined temperature, the control circuit 11 controls the air conditioning system 20 as a process for the abnormality of the temperature so as to lower the temperature to less than the predetermined temperature (SA41).

The configuration described in the present embodiment can provide advantages below. In the wireless power supply system 1, the transmitting and receiving state of electromagnetic waves transmitted from the power transmitting antenna 13 of the vehicle-side system 3 to the power receiving antenna 4 of the headset 2 is monitored, and the monitoring result is notified. Thereby, the driver can ascertain whether or not the transmission and reception of the electromagnetic waves is stable. Even when the transmitting or receiving state of the electromagnetic wave becomes unstable, it is possible for the driver to grasp the fact and stabilize the transmitting or receiving state of the electromagnetic waves, and to measure the brain activity of the driver stably. In addition, the wireless power supplying from the vehicle-side system 3 to the headset 2 eliminates the necessity of mounting a battery in the headset 2, the weight of the headset 2 can be reduced, and practicality can be enhanced.

When the reception intensity of the electromagnetic wave in the power receiving antenna 4 changes and the state in which the reception intensity of the electromagnetic wave in the power receiving antenna 4 is equal to or lower than a predetermined intensity continues for a predetermined period of time, it is determined that the receiving state of the electromagnetic wave by the power receiving antenna 4 becomes unstable. It is possible to determine whether or not to notify that the reception of the electromagnetic waves has become unstable based on the period of time during which the state where the reception intensity in the power receiving antenna 4 is kept at a predetermined intensity or less continues.

The posture of the driver when the receiving state of the electromagnetic wave is stable is stored as a normal posture in a storage. When it is determined that the receiving state of electromagnetic waves is unstable, notification information prompting to return the current posture to the normal posture stored in the storage is notified. The receiving state of the electromagnetic wave can be thus promptly stabilized.

When the reception intensity of the electromagnetic wave in the monitoring power receiving antenna 14 changes and the state where the reception intensity of the electromagnetic wave in the monitoring power receiving antenna 14 is equal to or less than a predetermined intensity continues for a predetermined period of time, it is determined that the transmission state of the electromagnetic wave from the power transmitting antenna 13 becomes unstable. It is possible to determine whether or not to notify that the transmission of electromagnetic waves has become unstable based on the period of time during which the state where the reception intensity in the monitoring power receiving antenna 14 is kept at a predetermined intensity or less continues.

When it is determined that the driver is in a non-awake state as an abnormality of the brain activity of the driver, a process of awakening the driver such as giving a stimulus to the driver is performed. It is possible to appropriately deal with the driver's being in a non-awake state; it is possible to prevent occurrence of a trouble due to the driver's non-awake state in advance.

When it is determined that the temperature has reached a predetermined temperature as the abnormality of the temperature of the brain sensors 8a to 8n, the air conditioning system 20 is controlled to perform the process of lowering the temperature to less than a predetermined temperature. It is possible to appropriately deal with the fact that the temperature has reached the predetermined temperature and occurrence of troubles due to the temperature rise of the brain sensors 8a to 8n can be avoided in advance.

Although the present disclosure has been described in accordance with the embodiment, it is understood that the present disclosure is not limited to the embodiment and its configuration. The present disclosure may cover the various modification examples or variations within the equivalent scope. In addition, while the various elements are shown in various combinations or configurations, which are just examples, other combinations or configurations, including more, less or only a single element, are also within the spirit and scope of the present disclosure.

Both of or one of the brain activity measurement data and the temperature measurement data may be transferred, e.g., from the vehicle-side system 3, to an external device or instrument such as a portable terminal that be brought into the vehicle by the driver of the vehicle; the brain activity of the driver and/or the temperature of the brain sensors 8a to 8n may be managed by the external device or instrument. That is, the portable terminal may be provided with a control circuit that includes all or part of the sections in the control circuit 11 in the vehicle-side system 3.

When it is determined that the driver is in a non-awake state as an abnormality in brain activity of the driver, a process of awakening the driver is performed. In addition thereto, the vehicle may be forcibly stopped in a safe area by cooperating with a vehicle control system that controls acceleration, deceleration, or steering.

Furthermore, the headset 2 may measure, detect, or sense any other activity of the driver by installing or using a corresponding sensor that is actuated using the received electromagnetic wave.

It is noted that additional description relating to a configuration of a control circuit is made below. Although the above embodiment describes a configuration of a control circuit (i.e., each of the control circuit 7 and the control circuit 11), another configuration of such a control circuit may be employed, as summarized below.

A control circuit, which may be also referred to as a controller or an electronic control unit, may further include an interface communicating with an external apparatus, a storage, and an internal communication line connecting the foregoing components to each other and may be combined with another control circuit.

Such a control circuit provides a plurality of functions and may include sections to provide the respective functions In addition, the sequence (described above) executed by a control circuit similarly includes sections, e.g., each represented as SA1, SA2, SB1, or the like. Such sections may be included in not only one control circuit but also may be divided to be included in two or more control circuits (i.e., included in at least one control circuit). Several sections may be combined into a single section; one section may be divided into several sections. Each section may be also referred to or achieved as a processor, controller, device, module, or the like.

Furthermore, an individual one of the sections, processors, or the like included in at least one control circuit, or an individual control circuit of the at least one control circuit may be achieved by using or by including (i) at least one hardware circuit including analog circuit and/or digital circuit, or (ii) at least one processing unit such as a CPU in a computer along with memory storing instructions as a non-transitory tangible computer-readable storage medium storing instructions of program executed by the CPU, or (iii) a combination of the at least one hardware circuit and the at least one processing unit along with memory storing instruction, to thereby provide the functions.

For reference to further explain features of the present disclosure, a comparative technique is described as follows. There is provided a system that monitors the state of a driver and performs warning and/or driving assistance when detecting the deterioration in the driving ability of the driver, and prevents the occurrence of traffic accidents. For example, a configuration is disclosed which detects the line of sight of a driver with a sight line sensor and the rotation angle of the steering wheel with a rotation angle sensor to monitor the state of the driver.

There is assumed a technique measuring the brain activity while the driver is driving and utilizing the measurement result for safe driving. In such a configuration, a headset having a brain sensor is attached to the head of the driver to transmit a brain activity measurement data indicating the measurement result of the brain activity of the driver, while upon receiving the measurement result, the vehicle-side system analyzes it to monitor driver's brain activity. In this case, since the headset is attached to the head of the driver, it is desirable to wirelessly perform (i) power supply to the brain sensor and (ii) transmission and reception of brain activity measurement data, in consideration of wearability of the driver. The configuration wirelessly supplying the power to the brain sensor may be achieved by providing a power transmitting antenna that transmits electromagnetic waves in the vehicle-side system, and providing a power receiving antenna that receives the electromagnetic waves in the headset, under the state stabilizing the transmission and reception of electromagnetic waves.

Since the power receiving antenna is provided in the headset, when the driver moves their head, the relative position between the power transmitting antenna and the power receiving antenna changes; this may cause the receiving state of the electromagnetic wave by the power receiving antenna to become unstable. Also, an abnormality occurring on the power transmission side (i.e., the vehicle-side system) may cause the transmitting state of the electromagnetic wave from the power transmitting antenna to become unstable. As a result, when the transmitting or receiving state of the electromagnetic waves becomes unstable, there is a concern that it may be difficult to stably measure the brain activity of the driver.

It is thus desired to provide a wireless power supply system that enables the driver to appropriately respond to measure stably the brain activity of the driver even if the transmitting or receiving state of electromagnetic waves becomes unstable.

Aspects of the disclosure described herein are set forth in the following clauses.

According to a first aspect of the present disclosure, a wireless power supply system is provided to include a headset, a vehicle-side system, a transmission control section, a power transmission and reception monitoring section, and a notification control section. The headset, which is attached to a head of a driver of a vehicle, is configured (i) to generate an electric power by using an electromagnetic wave received by a power receiving antenna, (ii) to actuate a brain sensor with the generated electric power to measure a brain activity of the driver, and (iii) to wirelessly transmit brain activity measurement data indicating a measurement result. The vehicle-side system, which is provided to the vehicle, is configured (i) to transmit the electromagnetic wave from a power transmitting antenna fixedly provided to the vehicle, (ii) to wirelessly receive the brain activity measurement data from the headset, and (iii) to monitor a brain activity of the driver by using the received brain activity measurement data. The transmission control section is configured to control transmission of the electromagnetic wave from the power transmitting antenna. The power transmission and reception monitoring section is configured to monitor a transmitting state or a receiving state of the electromagnetic wave to provide a monitoring result. The notification control section configured to notify the monitoring result of the transmitting or receiving state of the electromagnetic wave by the power transmission and reception monitoring section by using a notification apparatus.

Since the transmitting or receiving state of the electromagnetic wave from the power transmitting antenna of the vehicle-side system to the power receiving antenna of the headset has been monitored; the monitoring result of the transmitting or receiving state of the electromagnetic wave is notified, the driver can grasp whether the transmitting or receiving state of the electromagnetic wave is stable or not. As a result, even when the transmitting or receiving state of the electromagnetic wave becomes unstable, the driver can grasp the fact so as to stabilize the transmitting or receiving state of the electromagnetic wave, thereby stably measuring the brain activity of the driver (i.e., predetermined measured, sensed, or detected driver's activity).

In addition, as a second aspect, a wireless power supply system is provided to include the headset of the first aspect, the vehicle-side system of the first aspect, and at least one control circuit. The at least one control circuit is configured to control transmission of the electromagnetic wave from the power transmitting antenna in the vehicle-side system, to monitor a transmitting state of the electromagnetic wave in the power transmitting antenna in the vehicle-side system or a receiving state of the electromagnetic wave in the power receiving antenna in the headset, to provide a monitoring result, and to notify the monitoring result of the transmitting state or the receiving state of the electromagnetic wave by using a notification apparatus to the driver who is enabled to respond based on the notified monitoring result.

Further, as an optional aspect of the second aspect, in the wireless power supply system, an individual control circuit of the at least one control circuit may be configured to include (i) at least one hardware circuit, or (ii) at least one central processing unit along with memory storing instructions, or (iii) a combination of (a) the at least one hardware circuit and (b) the at least one central processing unit along with memory.

Furthermore, as another optional aspect of the second aspect, in the wireless power supply system, the at least one control circuit may be configured by using at least one processor, wherein an individual processor of the at least one processor may be configured to include (i) at least one hardware circuit, or (ii) at least one central processing unit along with memory storing instructions, or (iii) a combination of (a) the at least one hardware circuit and (b) the at least one central processing unit along with memory.

What is claimed is:

1. A wireless power supply system comprising:
   a headset attached to a head of a driver of a vehicle, the headset being configured (i) to generate an electric power by using an electromagnetic wave received by a power receiving antenna, (ii) to actuate a brain sensor with the generated electric power to measure a brain activity of the driver, and (iii) to transmit brain activity measurement data indicating a measurement result;
   a vehicle-side system provided to the vehicle, the vehicle-side system being configured (i) to transmit the electromagnetic wave from a power transmitting antenna fixedly provided to the vehicle, (ii) to receive the brain activity measurement data from the headset, and (iii) to monitor a brain activity of the driver by using the received brain activity measurement data; and
   a controller including:
      a transmission control section configured to control transmission of the electromagnetic wave from the power transmitting antenna,
      a power transmission and reception monitoring section configured to monitor a transmitting state or a receiving state of the electromagnetic wave to provide a monitoring result, and
      a notification control section configured to notify the monitoring result of the transmitting state or the receiving state of the electromagnetic wave by the power transmission and reception monitoring section by using a notification apparatus.

2. The wireless power supply system according to claim 1, wherein:
   the power transmission and reception monitoring section includes a power reception monitoring section configured to monitor a receiving state of the electromagnetic wave by the power receiving antenna, to provide a monitoring result; and the notification control section notifies the monitoring result of the receiving state of the electromagnetic wave by using the notification apparatus.

3. The wireless power supply system according to claim 2, wherein
in response to that a state where a reception intensity of the electromagnetic wave is less than or equal to a predetermined intensity continues for a predetermined period of time, the power reception monitoring section determines that the receiving state of the electromagnetic wave is unstable.

4. The wireless power supply system according to claim 3, wherein the controller further includes:
a posture detection section configured to detect a posture of the driver; and
a normal posture storage section configured to store, as a normal posture, a posture of the driver when the power reception monitoring section determines that the receiving state of the electromagnetic wave is stable, wherein
in response to that the power reception monitoring section determines that the receiving state of the electromagnetic wave is unstable, the notification control section notifies notification information that prompts to return a current posture to the normal posture by using the notification apparatus.

5. The wireless power supply system according to claim 1, wherein:
the power transmission and reception monitoring section includes a power transmission monitoring section configured to monitor a transmitting state of the electromagnetic wave by the power transmitting antenna to provide a monitoring result; and
the notification control section notifies the monitoring result of the transmitting state of the electromagnetic wave by using the notification apparatus.

6. The wireless power supply system according to claim 5, further comprising:
a monitoring power receiving antenna fixedly provided to the vehicle, wherein
the power transmission monitoring section determines that the transmitting state of the electromagnetic wave is unstable in response to that a state where a reception intensity of the electromagnetic wave received by the monitoring power receiving antenna is equal to or less than a predetermined intensity continues for a predetermined period of time.

7. The wireless power supply system according to claim 1, wherein the controller further includes:
a driver monitoring section configured to monitor a state of the driver to provide a monitoring result, wherein
the transmission control section controls a transmission of the electromagnetic wave from the power transmitting antenna based on the monitoring result by the driver monitoring section.

8. The wireless power supply system according to claim 1, wherein the controller further includes:
a vehicle travel monitoring section configured to monitor a travel state of the vehicle to provide a monitoring result, wherein
the transmission control section controls a transmission of the electromagnetic wave from the power transmitting antenna based on the monitoring result of the vehicle travel monitoring section.

9. The wireless power supply system according to claim 1, wherein the controller further includes:
a brain activity determination section configured (i) to determine a brain activity of the driver based on the brain activity measurement data and (ii) to perform a process for an abnormality of the brain activity of the driver in response to determining an abnormality of the brain activity of the driver.

10. The wireless power supply system according to claim 1, wherein:
in response to determining a non-awake state of the driver as an abnormality of the brain activity of the driver, the brain activity determination section performs a process to awake the driver as a process for the abnormality of the brain activity.

11. The wireless power supply system according to claim 1, wherein the controller further includes:
a temperature determination section configured to determine an abnormality of a temperature of the brain sensor, wherein:
the headset measures a temperature of the brain sensor using a temperature sensor to provide a measurement result and transmits a temperature measurement data indicating the measurement result;
upon receiving the temperature measurement data from the headset, the vehicle-side system monitors the temperature of the brain sensor based on the received temperature measurement data to provide a monitoring result; and
in response to determining the abnormality of the temperature of the brain sensor based on the monitoring result, the temperature determination section performs a process for the abnormality of the temperature.

12. The wireless power supply system according to claim 11, wherein the controller further includes:
an air conditioning control section configured to control air conditioning, wherein
when determining the temperature of the brain sensor reaching a predetermined temperature as a temperature abnormality, the temperature determination section performs a process for lowering the temperature of the brain sensor to less than a predetermined temperature by using the air conditioning control section as the process for the abnormality of the temperature.

13. The wireless power supply system according to claim 1, wherein
the headset includes a plurality of the brain sensors and selectively actuates the plurality of the brain sensors.

14. A non-transitory tangible computer-readable storage medium containing instructions executed by a computer for a vehicle-side system that is included in a wireless power supply system together with a headset, the headset being attached to a head of a driver of a vehicle, the headset being configured (i) to generate an electric power by using an electromagnetic wave received by a power receiving antenna, (ii) to actuate a brain sensor with the generated electric power to measure a brain activity of the driver, and (iii) to transmit a brain activity measurement data indicating a measurement result,
the vehicle-side system being provided to the vehicle, the vehicle-side system being configured (i) to transmit the electromagnetic wave from a power transmitting antenna fixedly provided to the vehicle, (ii) to receive the brain activity measurement data from the headset, and (iii) to monitor a brain activity of the driver by using the received brain activity measurement data, the instructions for implementing:
monitoring a transmitting state or a receiving state of an electromagnetic wave to provide a monitoring result; and
notifying the monitoring result of the transmitting state or the receiving state of an electromagnetic wave by using a notification apparatus.

15. A wireless power supply system comprising:
a headset attached to a head of a driver of a vehicle, the headset being configured (i) to generate an electric power by using an electromagnetic wave received by a power receiving antenna, (ii) to actuate a brain sensor with the generated electric power to measure a brain activity of the driver, and (iii) to wirelessly transmit a brain activity measurement data indicating a measurement result;
a vehicle-side system provided to the vehicle, the vehicle-side system being configured (i) to transmit the electromagnetic wave from a power transmitting antenna fixedly provided to the vehicle, (ii) to wirelessly receive the brain activity measurement data from the headset, and (iii) to monitor a brain activity of the driver by using the received brain activity measurement data; and
at least one control circuit configured
to control transmission of the electromagnetic wave from the power transmitting antenna in the vehicle-side system,
to monitor a transmitting state of the electromagnetic wave in the power transmitting antenna in the vehicle-side system or a receiving state of the electromagnetic wave in the power receiving antenna in the headset, to provide a monitoring result, and
to notify the monitoring result of the transmitting state or the receiving state of the electromagnetic wave by using a notification apparatus to the driver who is enabled to respond based on the notified monitoring result.

16. The wireless power supply system according to claim 15, wherein
the vehicle-side system comprises the at least one control circuit.

17. The wireless power supply system according to claim 15, wherein
the at least one control circuit is provided in a portable terminal brought into the vehicle by the driver of the vehicle, the portable terminal being configured to communicate with the vehicle-side system.

18. The wireless power supply system according to claim 15, wherein
an individual control circuit of the at least one control circuit is provided either (i) in the vehicle-side system or (ii) in a portable terminal brought into the vehicle by the driver of the vehicle, the portable terminal being configured to communicate with the vehicle-side system.

* * * * *